United States Patent [19]

Johns

[11] Patent Number: 4,513,739

[45] Date of Patent: Apr. 30, 1985

[54] WOUND DRESSING

[75] Inventor: Owen L. Johns, Clearwater, Fla.

[73] Assignee: Howmedica, Inc., New York, N.Y.

[21] Appl. No.: 466,770

[22] Filed: Feb. 15, 1983

[51] Int. Cl.³ .............................................. A61L 15/00
[52] U.S. Cl. ..................................... 128/156; 128/157
[58] Field of Search ................... 604/328; 128/132 D, 128/1, 132 R, 156, 155, 157

[56] References Cited

U.S. PATENT DOCUMENTS

| | | | |
|---|---|---|---|
| 3,260,260 | 7/1966 | Questel | 128/132 D |
| 3,367,329 | 2/1968 | Dibelius | 128/156 |
| 3,645,835 | 2/1972 | Hodgson | 161/146 |
| 3,811,438 | 5/1974 | Economou | 128/156 |
| 3,885,559 | 5/1975 | Economou | 128/156 |
| 3,989,040 | 11/1976 | Lofgren | 128/132 D |
| 4,265,234 | 5/1981 | Schaar | 128/156 |
| 4,374,520 | 2/1983 | Grossman | 128/132 D |

*Primary Examiner*—John D. Yasko
*Assistant Examiner*—Christa K. Scott
*Attorney, Agent, or Firm*—Charles J. Knuth; Peter C. Richardson; Harold W. Ordway

[57] ABSTRACT

An external wound dressing comprising a first layer of backing sheet material coated on one face with biocompatible adhesive; a second layer of protective sheet material covering the first layer in releasable contact with the adhesive, the second layer having means for separation in one or more sections from the first layer; and release-retarding means along one or a pair of opposed edges of the dressing to require a greater force to separate the layers at the edge or edges than at the remainder of the contact area.

17 Claims, 11 Drawing Figures

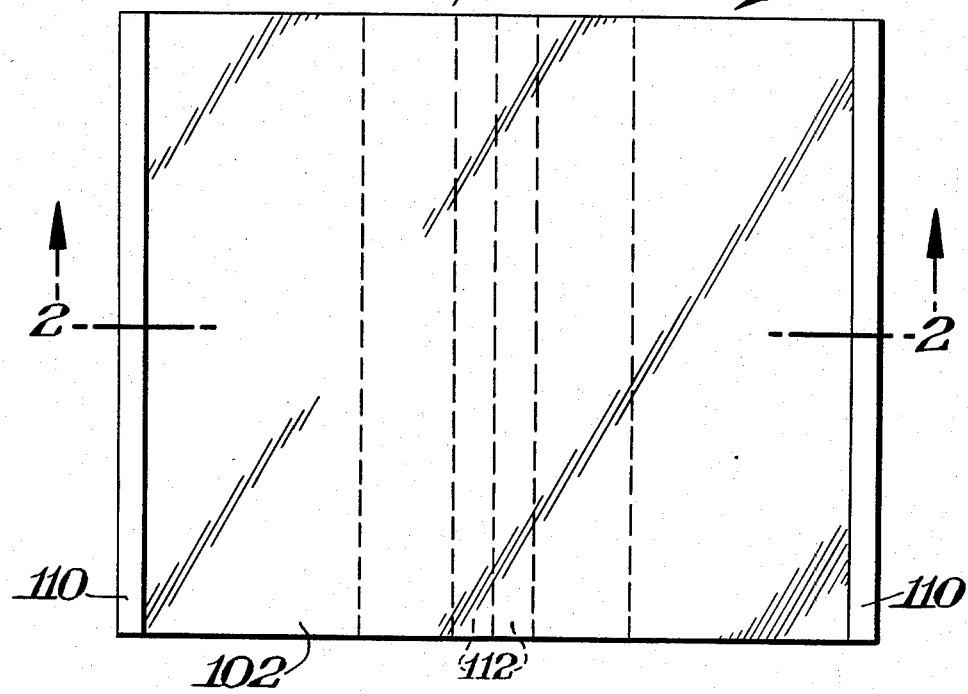
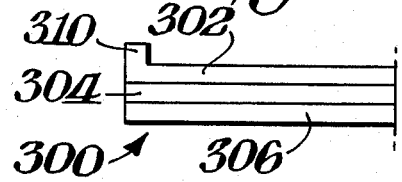 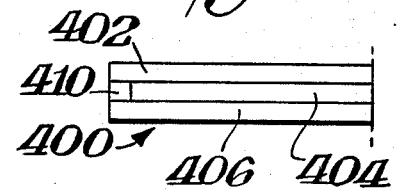
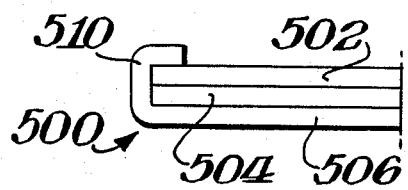 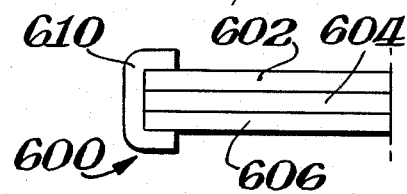

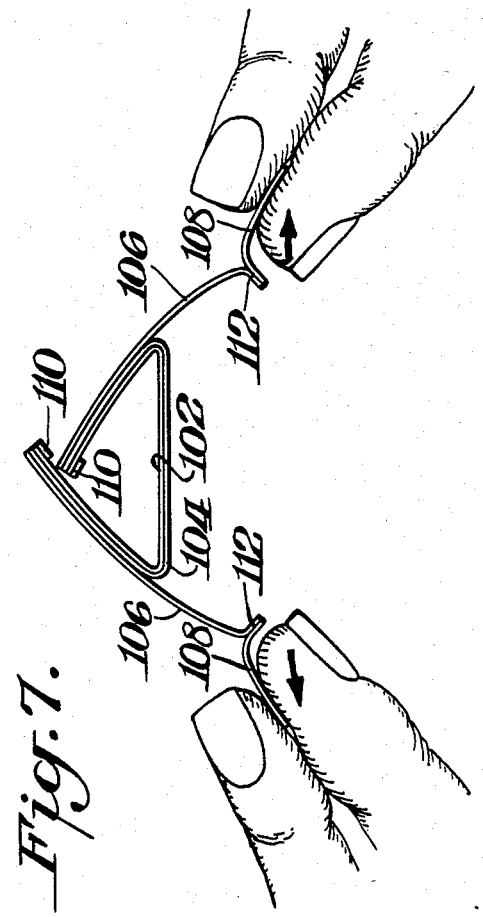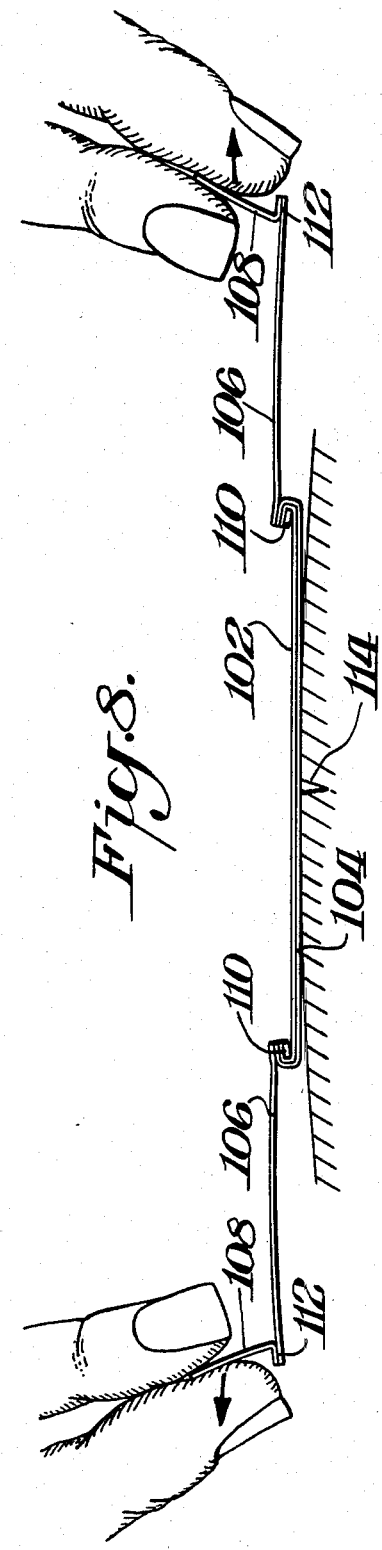

WOUND DRESSING

BACKGROUND OF THE INVENTION

The present invention concerns an improved medical dressing for protecting external wounds of mammals, especially humans.

A wide variety of dressings has been proposed for the protection and healing both of accidental wounds such as burns and abrasions and of deliberate cuts to the skin such as surgical incisions, as well as for the treatment of dermatological skin disorders.

Of particular importance are those dressings which are selectively permeable to oxygen and water vapor but impervious to liquids, infectious microorganisms and body salts. With some of these dressings, such as those disclosed in U.S. Pat. No. 3,367,329, adhesion to the skin is provided only at the periphery of the dressing, while in others, such as those of U.S. Pat. No. 3,645,835, pressure-sensitive adhesive coats substantially the entire body-adhering portion of the dressing. Numerous variations of the latter dressing are presently in use, but all of these variations require several steps to remove the release paper protecting the adhesive side of the dressing and/or to tear out or cut off ungummed edges. In addition, the dressings cannot be readily applied to the intended skin area without contamination of the the dressing from contact of the adhesive surface with the hand of the applicant.

It is therefore a primary objective of the present invention to provide an improved dressing for external wounds which not only is easy to apply but also precludes contaminating contact by the applicant of the adhesive side of the dressing.

A bandage with the adhesive in the form of layers alternatively spaced with regions of lesser adhesiveness therebetween to reduce pain on removal from the skin is disclosed in U.S. Pat. No. 3,811,438 and 3,885,559.

SUMMARY OF THE INVENTION

Such an improved external wound dressing comprises a first layer of backing sheet material having biocompatible adhesive coating on a first face thereof; a second layer of protective sheet material covering the first layer in releasable contact with the adhesive, the second layer having means for its separation in one or more sections from the first layer; and release-retarding means along one edge or a pair of opposed edges of the dressing to require a greater force to separate the layers at the edge or edges than at the remainder of the contacting area.

The release-retarding means may be provided in numerous ways. It may comprise, for example, a strip of flexible tape attached to the second face of the backing material of the first layer; a strip of the backing material of the first layer having a thickness greater than that of the remainder of the backing material; a strip of adhesive on the first face of the backing material of the first layer of greater tenacity than the adhesive coating the remainder of the backing material; a strip of the second layer extending over the dressing edge and attached to the second face of the backing material of the first layer; or a strip of flexible sheet material attached to the second layer and to the second face of the backing material of the first layer.

To effectively dispose of moisture from the wound site, the dressing preferably has a breathable first layer, and the dressing adhesive might also be water absorbent.

Preferably, the backing material of the breathable first layer is transparent polyurethane film while the second layer is silicone release coated paper. The dressing is preferably in rectangular form with release-retarding means along a pair of opposed edges of the dressing and with the second layer comprising two essentially equal sections, each of which has a pull tab attached to the inside edge thereof. In dressings with release-retarding means along a single edge, the second layer may comprise a single section with a pull tab attached to each of the first and second layers at the edge of the dressing opposite the release-retarding means.

The present invention further contemplates a method of protecting an external wound which comprises application of the instant dressing thereto.

BRIEF DESCRIPTION OF THE DRAWINGS

Novel features and advantages of the present invention in addition to those mentioned above will become apparent from a reading of the following detailed description in conjunction with the accompanying drawings wherein:

FIG. 1 is a top plan view of a wound dressing according to the present invention;

FIG. 2 is a cross-sectional view of the wound dressing taken along line 2—2 of FIG. 1;

FIGS. 3–6 are enlarged fragmented portions in side elevation of variations of the wound dressing of FIG. 1;

FIG. 7 is a side elevational view of the wound dressing of FIGS. 1 and 2 illustrating the release layer being separated from the backing layer;

FIG. 8 is a side elevational view at the point of placing the wound dressing of FIGS. 1 and 2 on a wound;

DETAILED DESCRIPTION OF THE INVENTION

Figure 9:
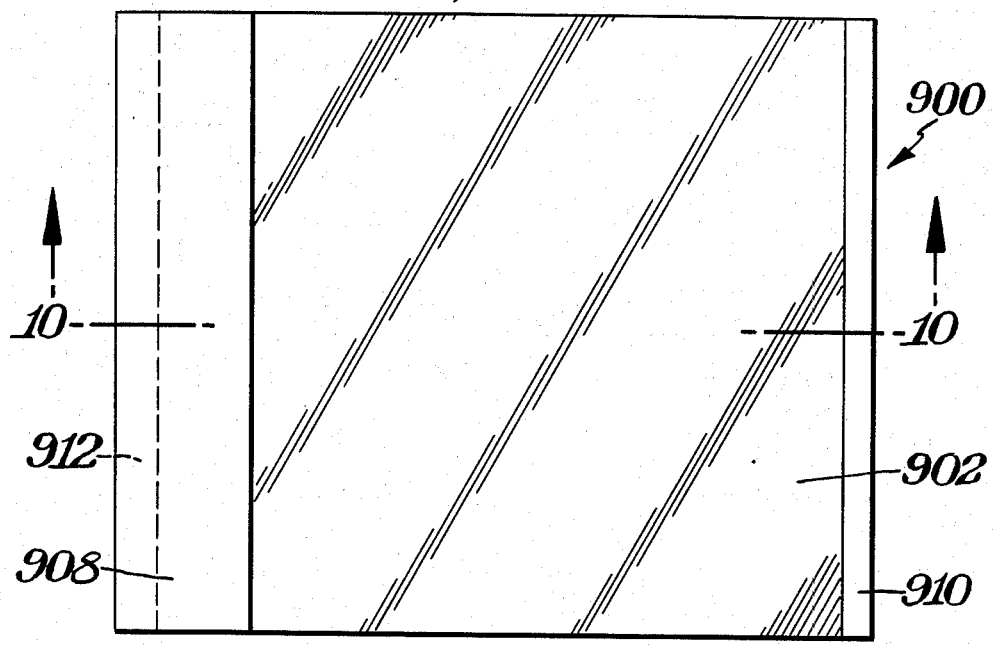
FIG. 9 is a top plan view of a second embodiment of the wound dressing according to the present invention.

An embodiment of the external wound dressing of the present invention is shown in FIGS. 1 and 2.

This dressing 100, rectangular in shape, comprises a first or backing layer of a backing sheet material 102 coated on one face with a biocompatible adhesive 104 which, in turn, is protected by a second or release layer 106 in releasible contact with adhesive 104. Release layer 106 consists of two essentially equal sections, each with an attached pull tab 108 to assist in the separation of release layer 106 from adhesive 104. Dressing 100 further has a strip 110 of flexible tape attached to the second face of backing material 102 along each of the two opposed edges of the dressing 100, strips 110 serving as a means for retarding the separation of release layer 106 from adhesive 104 at these edges. The attachment of tab 108 to each section of release layer 106 is along the inside edge 112 of the section.

Backing material 102 may be of any sheet material which is suitable for covering a skin wound. Preferably, however, backing material 102 is a transparent or translucent plastic film which is resistant to water and is breathable, i.e., impermeable to liquids and microbiological contamination but permeable to water vapor and oxygen. Likewise adhesive 104, which preferably coats substantially the entire first face of backing material 102, is preferably a pressure-sensitive adhesive having similar transparency and permeability characteristics. Such suitable films and adhesives and their preparations are described, for example, in U.S. Pat. No. 3,645,835, the contents of which is incorporated herein by reference. These adhesive coated films should preferably have a water vapor transmission rate of at least 250 g/m$^2$/24 hrs (40° C., 80% RH). Especially preferred are such adhesive coated films with a transmission rate of about 400 to 500 g/m$^2$/24 hrs in which the backing material is a transparent polyurethane film of about 0.5 to 2 mils (13 to 51 microns) thickness coated with an about 1 mil (25 micron) layer of pressure-sensitive acrylic ester copolymer adhesive.

Within the scope of the present invention is a wound dressing in which the breathable first layer of adhesive coated plastic film is replaced by a backing layer of an impermeable film with moisture-absorbing adhesive mixtures having a moisture absorption rate equal to or greater than the permeability rate of the breathable layer. Such moisture-absorbing mixtures could be in the form of a single adhesive layer contacting the skin or of a second layer coated with an adhesive such as used with the breathable film. Also contemplated is a wound dressing which combines the breathable and moisture-absorbing features.

Release layer 106 may be of any sheet material such as paper, polyethylene or polypropylene which will adequately protect and be properly released from adhesive 104. A suitable release material, for example, is a 40 to 75 pound basis weight paper coated on one or both sides with a suitable finish such as clay and with a release agent such as silicone. The thickness of release layer 106 will normally be from about 2 to 6 mils (51 to 152 microns). Pull tab 108 attached to the inside edge 112 of each of the two sections of release layer 106 may be of the same material and integral with layer 106. Alternatively, pull tab 108 may be of another suitable sheet material and attached to release layer 106 by any suitable manner such as with pressure-sensitive adhesive. Similarly, pull tab 108 might also conveniently take other forms such as a string or strip.

Release-retarding strips 110, as explained in greater detail hereinbelow, facilitate the application of dressing 100 to the wound area and, further, prevent its contamination by the applicant. These strips 110 should be of such width and thickness that dressing 100 is firmly supported while it is being applied to the wound. Thus, strips 110 will normally have a width of from about 1 to 3 mm and a thickness of from about 1 to 4 mils (25 to 102 microns). Strips 110 may be fabricated from any flexible sheet material and attached in any suitable manner to backing material 102; preferably, strips 110 are of plastic tape attached to backing material 102 by pressure-sensitive adhesive.

The release-retarding means of the present invention may take various forms other than the strip 110 of FIGS. 1 and 2, certain variations of the means being shown in FIGS. 3-6.

In FIG. 3, this means comprises a strip 310 of backing material 302 having a thickness greater than that of, and integral with, the remainder of backing material 302. Again, strip 310 will normally be from about 1 to 3 mm wide and have a thickness of from about 1.2 to 3 times that of the remainder of backing material 302. Adhesive 304 and release layer 306 of wound dressing 300 may be the same as hereinbefore described.

In FIG. 4, the release-retarding means for wound dressing 400 is provided by a strip of adhesive 410 having a greater tenacity, and therefore a greater resistance to separation from release layer 406, than adhesive 404 coating the remainder of backing material 402. Any combination of biocompatible adhesives satisfying this requirement may be used. For example, backing adhesive 404 may be an acrylic ester copolymer based adhesive while strip adhesive 410 may be a rubber based adhesive.

With wound dressing 500 of FIG. 5, the release-retarding means in the separation of release layer 506 from adhesive 504 is obtained by extending release layer 506 over the edge of dressing 500 and attaching it to the second face of backing material 502 in any suitable manner, such as with adhesive or by heat sealing. The width of the strip 510 of release layer 506 attached to backing material 502 will normally be from about 1 to 3 mm, the release layer 506, as indicated hereinbefore, normally having a thickness of from about 2 to 6 mils (51 to 152 microns).

In FIG. 6, the release-retarding means in the separation of release layer 606 from adhesive 604 of wound dressing 600 comprises a strip 610 of flexible sheet material attached to both release layer 606 and to the second face of backing material 602. Again, the attachment may be by any suitable means, such as with adhesive or by heat sealing. The strip 610 may be of any suitable flexible sheet material such as polyethylene film with a thickness of from about 1 to 6 mils (25 to 152 microns), and the width of strip 610 attached to backing material 602 may conveniently be from about 1 to 3 mm.

Release-retarding means other than those explicitly disclosed hereinbefore may be contemplated. For example, the release layer may have on each of the outside edges of its two sections a strip of the layer's surface in contact with the adhesive which provides more tack than the remainder of the contact surface. Such obvious variations are to be considered within the scope of the present invention.

In use, wound dressing 100 is removed from a standard sterile wrapping by the applicant, who then grasps a pull tab 108, attached to release layer 106 along inside edge 112, between the thumb and index finger of each of the hands. As shown in FIG. 7, when the applicant pulls the two tabs 108 away from each other, release layer 106 separates in its two sections from backing material 102 and its adhesive coating 104. The separation occurs with little resistance until it encounters strips 110. At this point, the separation stops, with backing material 102 still firmly attached to release layer 106, until a considerably increased separation force is applied. Thus, as shown in FIG. 8, release layer 106 may be pulled away from all but the extreme edges of the adhesive 104, and dressing 100 then carefully and easily applied to a wound 114 without wrinkling. A slight tug on each of pull tabs 108 frees the remainder of release layer 106, pull tab 108 remaining firmly attached to release layer 106 along inside edge 112, and dressing 100 is now firmly in place on wound 114 without finger contact with the adhesive 104, wrinkling of the dressing, use of scissors to remove extraneous tabs, or other complications.

Figure 10:
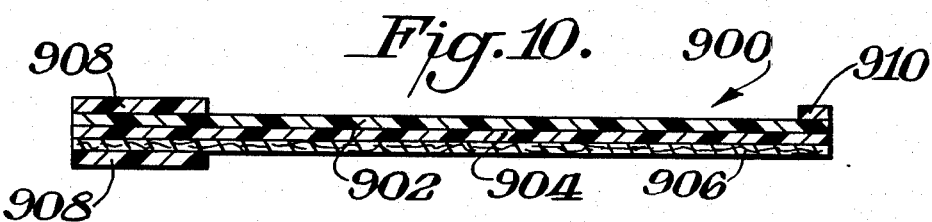
FIG. 10 is a cross-sectional view of the wound dressing taken along line 10—10 of FIG. 9.

A second embodiment of the external wound dressing of the present invention is shown in FIGS. 9 and 10, the dressing 900 suitably being fabricated of the same materials and having the various release-retarding means as disclosed for wound dressing 100. With this wound dressing 900, the release-retarding means, here shown as a strip 910, is attached to the second face of backing material 902 along a single edge and release layer 906, in releasable contact with adhesive 904, comprises a single section. This wound dressing 900 has a pull tab 908 attached to each of release layer 906 and backing material 902 along the edge 112 opposite release-retarding strip 910.

Figure 11:
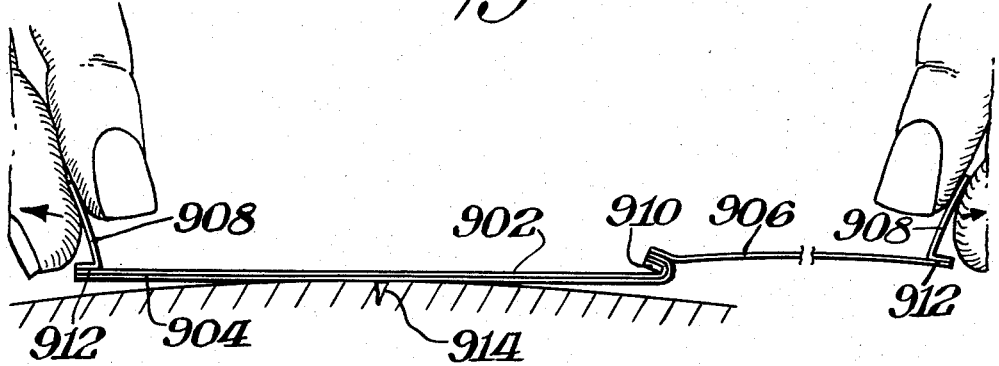
FIG. 11 is a side elevational view at the point of placing the wound dressing of FIGS. 9 and 10 on a wound.

Thus, as shown in FIG. 11, release layer 906 is separated from backing material 902 with its adhesive coating 904 by the applicant grasping a pull tab 908 in each of the hands and pulling the pull tabs 908 away from each other. The separation continues until it reaches release-retarding strip 910, where increased resistance to separation is encountered. Applicant then places the dressing 900 over and upon a wound 914, and finally separates release layer 906 by a gentle tug on pull tab 908 attached to release layer 906. Pull tab 908 attached to backing material 902 may be retained with the dressing; preferably, however, this pull tab 908 is releasably attached to backing layer 902 and may be separated by a simple tug.

I claim:

1. An external wound dressing, which comprises:
   (a) a first layer of backing sheet material having biocompatible adhesive coating on a first face thereof;
   (b) a second layer of protective sheet material covering said first layer in releasible contact with said adhesive, said second layer having means for separation in one or more sections from said first layer; and
   (c) release-retarding means along one edge or a pair of opposed edges of said dressing to require a greater force to separate said layers at said edges than at the remainder of the contacting area.

2. The dressing of claim 1 wherein said release-retarding means comprises a strip of flexible tape attached to the second face of said backing material.

3. The dressing of claim 2 wherein said attachment is by use of pressure-sensitive adhesive.

4. The dressing of claim 1 wherein said release-retarding means comprises a strip of said backing material having a thickness greater than that of the remainder of said backing material.

5. The dressing of claim 1 wherein said release-retarding means comprises a strip of adhesive on said backing material first face of greater tenacity than the adhesive coating the remainder of said backing material first face.

6. The dressing of claim 5 wherein said strip adhesive is rubber based and said remaining adhesive is acrylic ester copolymer.

7. The dressing of claim 1 wherein said release-retarding means comprises a strip of said second layer extending over said dressing edge and attached to the second face of said backing material.

8. The dressing of claim 1 wherein said release-retarding means comprises a strip of flexible sheet material attached to said second layer and to the second face of said backing material.

9. The dressing of claim 1 wherein said first layer is breathable.

10. The dressing of claim 9 wherein said backing material is transparent polyurethane film.

11. The dressing of claim 1 wherein said adhesive is water absorbent.

12. The dressing of claim 1 wherein said second layer is silicone release coated paper.

13. The dressing of claim 1 in rectangular form.

14. The dressing of claim 1 having release-retarding means along a pair of opposed edges of said dressing wherein said second layer comprises two essentially equal sections, each of said sections having a pull tab attached to the inside edge thereof.

15. The dressing of claim 1 having release-retarding means along one edge of said dressing wherein said second layer comprises a single section with a pull tab attached to each of said first and second layers at the edge of said dressing opposite said one edge.

16. A rectangular shaped external wound dressing, which comprises:
   (a) a breathable first layer of backing sheet material having biocompatible adhesive coating one face thereof;
   (b) a second layer of protective sheet material covering said first layer in releasible contact with said adhesive, said second layer comprising two essentially equal sections with each of said sections having a pull tab attached to the inside edge thereof for separation of said second layer from said first layer; and
   (c) a strip of pressure-sensitive tape attached to the second face of said backing material along a pair of opposed edges of said dressing, whereby a greater force is required to separate said layers at said edges than at the remainder of the contacting area.

17. A method of protecting an external wound, which comprises application of the dressing of claim 1 thereto.

* * * * *